US00PP15957P3

(12) United States Plant Patent
Eremin

(10) Patent No.: US PP15,957 P3
(45) Date of Patent: Sep. 13, 2005

(54) ***PRUNUS* PLANT NAMED 'VSV-1'**

(50) Latin Name: ***Prunus incana*×*Prunus tomentosa***
Varietal Denomination: VSV-1

(75) Inventor: Guennadi Eremin, Krymsk (RU)

(73) Assignee: Varieties International, LLC, Dundee, OR (US)

( * ) Notice: Subject to any disclaimer, the term of this patent is extended or adjusted under 35 U.S.C. 154(b) by 308 days.

(21) Appl. No.: 09/880,951

(22) Filed: Jan. 11, 2002

(65) Prior Publication Data

US 2003/0217399 P1 Nov. 20, 2003

(51) Int. Cl.[7] ..... A01H 5/00
(52) U.S. Cl. ..... Plt./183
(58) Field of Search ..... Plt./183

(56) References Cited

U.S. PATENT DOCUMENTS

PP14,126 P3 * 9/2003 Zaiger et al. ..... Plt./183
2003/0208807 P1 * 11/2003 Wolfram ..... Plt./183

OTHER PUBLICATIONS

UPOV ROM GTITM Computer Database, GTI JOUVE Retrieval Software 2003/05 citation for "VSV–1".*

* cited by examiner

*Primary Examiner*—Kent Bell
*Assistant Examiner*—W. C. Haas
(74) *Attorney, Agent, or Firm*—Webb Ziesenheim Logsdon Orkin & Hanson, P.C.

(57) ABSTRACT

A new and distinct rootstock variety of *Prunus* named 'VSV-1' that is characterized by vigor and strength, the ability to serve well as rootstock that is compatible with peach and plum, resistance to drought, cold and heat and the ability to propagate well by stool beds in addition to other methods. In combination these traits set the new cultivar apart from all other existing varieties of *Prunus* rootstock.

1 Drawing Sheet

Botanical classification: *Prunus incana*×*Prunus tomentosa.*
Varietal denomination: 'VSV-1'.

CROSS-REFERENCES TO RELATED APPLICATIONS

This application for the new invention *Prunus* Plant Named 'VSV-1' is co-pending with three other U.S. Plant Patent Applications: *Prunus* Plant Named 'VVA-1' (U.S. Plant patent application Ser. No. 09/880,952), *Prunus* Plant Named 'VSL-2' (U.S. Plant patent application Ser. No. 09/880,953), and *Prunus* Plant Named 'LC-52' (U.S. Plant patent application Ser. No. 09/880,950), each having the same filing date and inventor.

BACKGROUND OF THE INVENTION

The present invention relates to the new and distinct cultivar known botanically as a hybrid of *Prunus* and referred to hereinafter as 'VSV-1'. The new invention was bred by the inventor at the Breeding Station in Krymsk, Russia.

The breeding program at the Breeding Station was established in 1966 and funded by the government of the former Soviet Union for the purpose of producing new and improved *Prunus* cultivars that propagate well, have one central stem, few branches, and serve well as rootstock that is compatible with peach and plum.

In 1966 the inventor crossed the female parent *Prunus incana* (not patented) with the male parent *Prunus tomentosa* (not patented), producing an induced hybridization in a cultivated area of Krymsk, Russia. The resulting seedlings were observed and evaluated for ten years. In 1977 the inventor selected 'VSV-1' from these seedlings. The new cultivar originated as a single plant and is the result of a hybrid cross between the *Prunus incana* (not patented) and *Prunus tomentosa* (not patented).

The closest comparison plants are the parent plants. The characteristics that distinguish the new cultivar from *Prunus incana* are increased vigor, larger fruit, larger leaves and ease of propagation. The characteristics that distinguish the new cultivar from *Prunus tomentosa* are narrow leaves, small fruit, presence of stipules and strength of propagation. The distinguishing characteristics that make this cultivar unique from all other existing varieties of *Prunus* known to the inventor are vigor, the ability to propagate well by stool beds, resistance to drought, cold and heat and the ability to serve well as rootstock that is compatible with peach and plum.

'VSV-1' was first asexually propagated in 1977 by the inventor at the Breeding Station in Krymsk, Russia. The method used was softwood cuttings in vitro. The distinguishing traits have been determined stable and are reproduced true to type in successive generations.

SUMMARY OF THE INVENTION

The following traits have been repeatedly observed and represent the distinguishing characteristics of the new cultivar. These traits in combination distinguish 'VSV-1' from all other existing cultivars of *Prunus* hybrid known to the inventor. 'VSV-1' has not been tested under all possible conditions and phenotypic differences may be observed with variations in environmental, climatic, and cultural conditions, however, without any variance in genotype.

1. 'VSV-1' propagates well by stool beds in addition to other methods.
2. 'VSV-1' serves well as rootstock that is compatible with peach and plum.
3. 'VSV-1' is resistant to drought, cold and heat.

4. 'VSV-1' is strong and vigorous.
5. 'VSV-1' is hardy to minus 15° Centigrade.

BRIEF DESCRIPTION OF THE DRAWING

The photograph is an illustration of the new variety, VSV-1.

BOTANICAL DESCRIPTION OF THE PLANT

The following is a detailed botanical description of the new rootstock variety *Prunus* hybrid 'VSV-1'. Observations, measurements, values, and comparisons were collected in McMinnville, Oreg. from the inventor. The new variety was two (2) years old when described and was cultivated in a temperature variable environment. The foliage, flower and fruit exhibited by this cultivar are of no economic or commercial value, therefore comparisons and botanical descriptions of the foliage, fruit and flower are made for identification purposes only. Mature specimens, as well as bareroot specimens, were unavailable for photographing at the time this document was written. The color determinations are in accordance with The R.H.S. Colour Chart of The Royal Horticultural Society, London, England except where general color terms of ordinary dictionary significance are used.

Botanical classification: *Prunus incana*×*Prunus tomentosa*.
Parentage: *Prunus* 'VSV-1' is an induced hybrid that resulted from crossing the following plants.
- *Female parent.*—*Prunus incana* (not patented).
- *Male parent.*—*Prunus tomentosa* (not patented).

Type: Deciduous tree.
Use: 'VSV-1' serves as rootstock that is compatible with peach and plum.
Soil: Light, sandy soil required.
Light: Full sunlight.
Fruit bearing: No fruit observed on plants up to 3 years of age.
Crop time: Requires 3 years from rooted cutting to achieve finished product size ready to ship bareroot.
Dimensions at crop time: 2.5 m. in height and 2 m. in width.
Vigor: 50–60% of standard. *Prunus persica* is used as the standard (peach seedling).
Habit: Dwarf and generally upright with some arching branches.
Hardiness: USDA Zone 4A.
Cold tolerance: Excellent.
Heat tolerance: Excellent.
Propagation: Can be propagated by hardwood, softwood cuttings, meristem cuttings in vitro, and stool beds (layering).
Rooting habit: Fine and fibrous initially. After 1 year roots become fleshy and thick.
Time to initiate roots: 5–6 months to develop roots at 22–25° Centigrade.
Disease and insect resistance: Normal resistance to disease and insects.
Trunk:
- *Trunk dimensions.*—At 3 years the trunk is 4 cm. in diameter and 20 cm. in height (from soil level to first branch is 20 cm.).
- *Trunk bark surface.*—Glabrous surface.
- *Trunk bark color.*—201A.
- *Lenticels.*—Present in small amount.
- *Lenticel shape.*—Linear to lens shaped.
- *Lenticel color.*—198B.
- *Lenticel dimensions.*—Up to 4 mm. in length and 1 mm. in width.

Branches:
- *Branch surface.*—Pubescence on young emerging branches. Absent on other branches.
- *Branch color.*—201B.
- *Internode length.*—5–7 cm. between nodes.
- *Branching angle at emergence.*—60–65° and straight.
- *Branching habit.*—Medium branching.
- *Pubescence.*—Present on young branches.
- *Pubescence color.*—201C.
- *Lenticels* (*quantity*).—Present in small amounts on older branches and larger amount on young branches.
- *Lenticel shape.*—Linear to lens shape.
- *Lenticel color.*—198B.
- *Lenticel dimensions.*—2–3 mm. in length and 1 mm. in width.
- *Lenticel number.*—Approximately 9 per inch on rootstocks over 1 year old.

Leaves:
- *Arrangement.*—Alternate and whorled.
- *Leaf length.*—4.5 cm. in length.
- *Leaf width.*—2.5–3 cm. in width.
- *Leaf shape.*—Oblanceolate.
- *Leaf apex.*—Acuminate.
- *Leaf base.*—Cuneate.
- *Leaf color* (*adaxial surface*).—132B.
- *Leaf color* (*abaxial surface*).—132D.
- *Leaf surface* (*adaxial*).—Pubescent.
- *Leaf surface* (*abaxial*).—Pubescent.
- *Leaf margins.*—Crenulate.
- *Leaf division.*—Simple.
- *Petiole dimensions.*—4–5 mm. in length and 1 mm. in diameter.
- *Petiole color.*—131C.
- *Petiole surface.*—Pubescent.
- *Stipules.*—Present.
- *Stipule dimensions.*—2–2.5 mm. in length and 1 mm. in width.
- *Stipule color.*—132D.
- *Pubescence.*—Present on adaxial and abaxial surfaces.
- *Pubescence color.*—201D.
- *Venation pattern.*—Pinnate.
- *Vein color* (*adaxial and abaxial surfaces*).—131A.
- *Leaf texture.*—Wrinkled, and firm to leathery texture.
- *Leaf strength.*—Moderate strength.
- *Leaf appearance.*—Velvety on abaxial surface and dull on adaxial surface.

Fruit:
- *Maturity.*—70 to 75 days to mature.
- *Dates of picking.*—Not a fruit crop. Fruit has no commercial value.
- *Production.*—Moderately fruit bearing.
- *Fruit form.*—Globose.
- *Stem dimensions.*—4–5 mm. in length and 1 mm. in width.
- *Stem color.*—143B.
- *Skin color.*—45B.
- *Skin surface.*—Puberulent.
- *Lenticels.*—Absent.
- *Flesh color.*—61D.
- *Flesh texture.*—Juicy.
- *Flavor.*—Sour cherry.
- *Aroma.*—None.
- *Seed number.*—One drupe.

*Seed shape.*—Round.
*Seed color.*—164A.
*Seed dimensions.*—5–6 mm. in diameter and 5–6 mm. in length.
*Storage.*—None has been determined.
*Use.*—None has been determined.

Flower:
*Arrangement.*—Solitary.
*Flower shape.*—Rotate.
*Bud dimensions.*—3mm. in width and 3 mm. in length.
*Bud color.*—56D.
*Time of bloom.*—Flowers bloom at 1 year and last for 7–8 days.
*Flower diameter.*—2.5 cm. in diameter.
*Flower depth* (*throat*).—3 mm. in depth.
*Bloom quantity.*—50–60 flowers per branch.
*Number of petals.*—Five petals in number.
*Fused or unfused.*—Petals are unfused.
*Petal shape.*—Obovate.
*Petal margin.*—Entire and wavy.
*Flower color fully opened* (*upper and lower surfaces*) .—155C.
*Dimensions of peduncle.*—3–4 mm. in length and up to 1 mm. in width.
*Color of peduncle.*—143C.
*Surface of peduncle.*—Pubescent.
*Calyx dimensions.*—3 mm. in length and 2.5 mm. in width.
*Calyx surface.*—Minimal pubescence.
*Calyx color.*—146B.
*Number of sepals.*—Five sepals in number.
*Natural flowering season.*—Spring.
*Persistent or self-cleaning.*—Self-cleaning.
*Fragrance.*—None.

Reproductive organs:
*Stamen number.*—Polyandrous. 12–15 stamens and unequal lengths.
*Stamen color.*—155C.
*Anther.*—Round with stamen attached at center of dorsal surface.
*Anther color.*—20B.
*Anther dimensions.*—1 mm. in length and 1 mm. in width.
*Amount of pollen.*—Large amount.
*Color of pollen.*—20B.
*Pistil.*—One in number.
*Pistil color.*—1C.
*Pistil dimensions.*—4 mm. in length and 1 mm. in width.
*Style color.*—9A.
*Style dimensions.*—1 mm. in length and 0.50 mm. in width.
*Ovary dimensions.*—2 mm. in length and 2 mm. in width.
*Ovary color.*—155C.
*Ovary position.*—Superior.

I claim:

1. A new and distinct variety of *Prunus* plant named 'VSV-1' as herein described and illustrated.

* * * * *

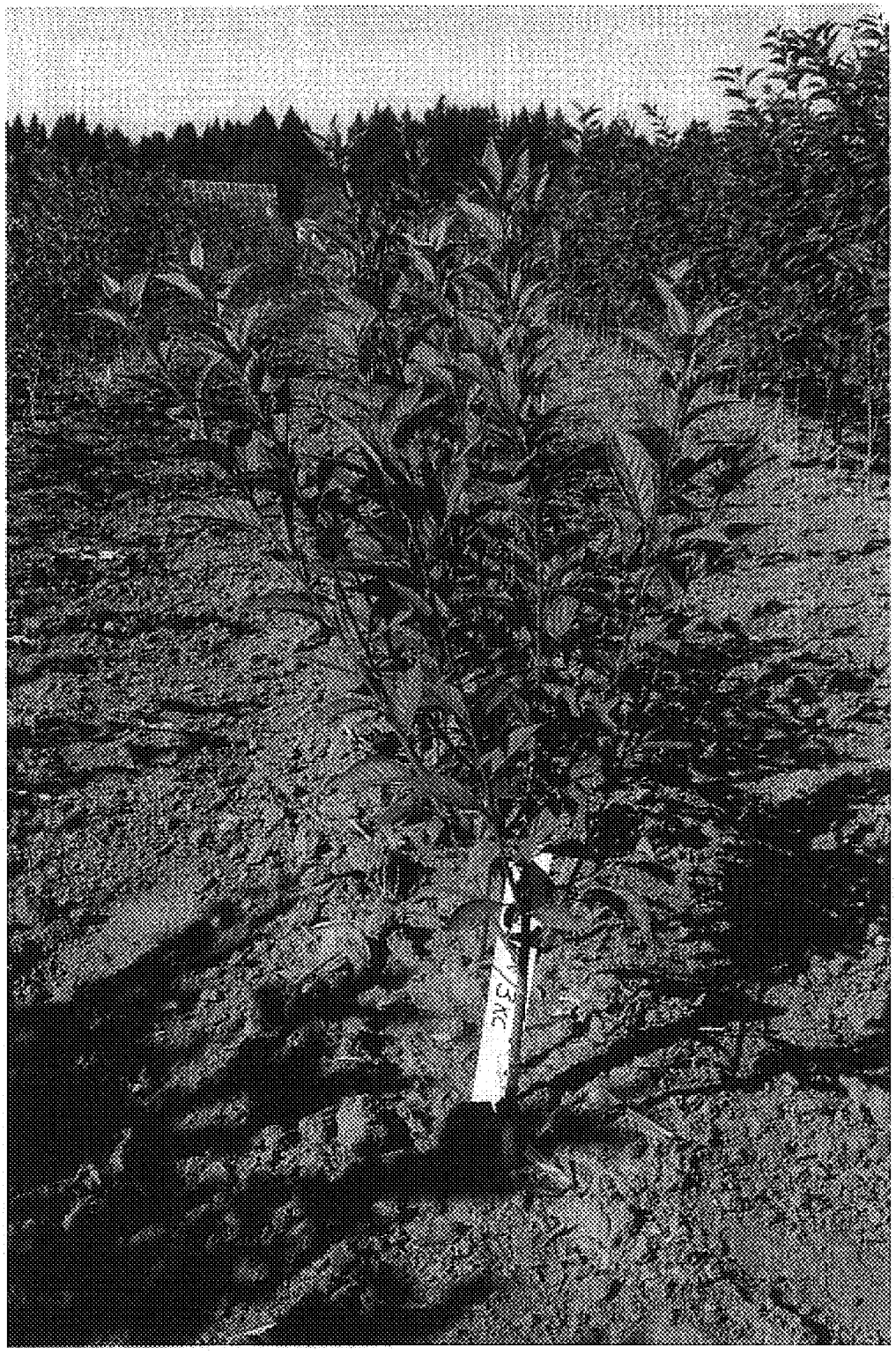
3MC